United States Patent
Ma

(10) Patent No.: US 11,192,814 B2
(45) Date of Patent: Dec. 7, 2021

(54) ON-SITE GENERATION OF ENERGY IN A MULTI-UNIT BUILDING

(71) Applicant: Morrison Zhu Goodman Realty Group LLC, Bronx, NY (US)

(72) Inventor: Mike Ma, Bronx, NY (US)

(73) Assignee: Morrison Zhu Goodman Realty Group LLC, Bronx, NY (US)

( * ) Notice: Subject to any disclaimer, the term of this patent is extended or adjusted under 35 U.S.C. 154(b) by 0 days.

(21) Appl. No.: 16/762,743

(22) PCT Filed: Nov. 8, 2018

(86) PCT No.: PCT/US2018/059736
§ 371 (c)(1),
(2) Date: May 8, 2020

(87) PCT Pub. No.: WO2019/094535
PCT Pub. Date: May 16, 2019

(65) Prior Publication Data
US 2021/0070645 A1 Mar. 11, 2021

Related U.S. Application Data

(60) Provisional application No. 62/585,371, filed on Nov. 13, 2017.

(51) Int. Cl.
| C02F 11/04 | (2006.01) |
| C02F 3/28 | (2006.01) |
| C12M 1/00 | (2006.01) |
| C02F 103/00 | (2006.01) |

(52) U.S. Cl.
CPC .......... *C02F 11/04* (2013.01); *C02F 3/2826* (2013.01); *C12M 43/08* (2013.01);
(Continued)

(58) Field of Classification Search
CPC .. C02F 11/04; C02F 3/2826; C02F 2209/008; C02F 2103/005; C02F 2201/009;
(Continued)

(56) References Cited

U.S. PATENT DOCUMENTS

| 6,106,716 A * | 8/2000 | Berkman ............... C02F 3/1242 |
| | | 210/603 |
| 2002/0079266 A1* | 6/2002 | Ainsworth ............. C12M 47/18 |
| | | 210/603 |

(Continued)

FOREIGN PATENT DOCUMENTS

| CN | 105296337 A | * | 6/2002 |
| CN | 101746938 A | * | 6/2010 |

(Continued)

*Primary Examiner* — Fred Prince
(74) *Attorney, Agent, or Firm* — Fish & Richardson P.C.

(57) ABSTRACT

A system includes an anaerobic digestion tank, a gas storage tank, a power generator, a power distribution system, and an electronic control system. The anaerobic digestion tank receives biological waste from a sewer line of a multi-unit building, and allows the received biological waste to be digested to produce a combustible gas. The gas storage tank stores the combustible gas. The power generator combusts the combustible gas to produce at least one of electrical power or heat. The power distribution system receives the electrical power from the power generator, stores at least some of the electrical power, and distributes at least some of the stored electrical power to one or more electrical devices. The electronic control system controls an operation of the system.

20 Claims, 4 Drawing Sheets

(52) U.S. Cl.
CPC .. *C02F 2103/005* (2013.01); *C02F 2201/009* (2013.01); *C02F 2209/006* (2013.01); *C02F 2209/008* (2013.01); *C02F 2303/10* (2013.01)

(58) Field of Classification Search
CPC .. C02F 2303/10; C02F 3/28; C02F 2209/006; C12M 43/08; C12M 21/04; Y02E 50/30; Y02W 10/10; Y02W 10/30; Y02W 10/20; Y02A 20/212
USPC .................................................. 210/603, 259
See application file for complete search history.

(56) References Cited

U.S. PATENT DOCUMENTS

| | | | | |
|---|---|---|---|---|
| 2002/0189173 A1* | 12/2002 | Staschik | ............... | C02F 9/00 |
| | | | | 52/79.1 |
| 2010/0206807 A1* | 8/2010 | Ripley | ............... | C02F 3/28 |
| | | | | 210/603 |
| 2013/0130346 A1* | 5/2013 | Hansen | ............... | B09B 3/00 |
| | | | | 435/167 |
| 2014/0209479 A1* | 7/2014 | Hoffmann | ............ | C02F 1/4674 |
| | | | | 205/743 |
| 2019/0112246 A1* | 4/2019 | MacGregor | ............ | C07C 31/04 |
| 2020/0283362 A1* | 9/2020 | MacGregor | ............ | C12M 43/00 |

FOREIGN PATENT DOCUMENTS

| | | | |
|---|---|---|---|
| CN | 202347010 U | * | 7/2012 |
| CN | 202675444 U | * | 1/2013 |
| WO | WO 2016202904 A1 | * | 12/2016 |

\* cited by examiner

ON-SITE GENERATION OF ENERGY IN A MULTI-UNIT BUILDING

CROSS-REFERENCE TO RELATED APPLICATION

This is the U.S. National Phase Application under 35 U.S.C. § 371 of International Patent Application No. PCT/US2018/059736 filed Nov. 8, 2018, which application claims priority under 35 U.S.C. § 119(e) to U.S. Provisional Application No. 62/585,371, filed Nov. 13, 2017, the disclosure of which is incorporated herein in its entirety. The International Application was published on May 19, 2019 as WO2019/094535 A1 under PCT article 21(3).

TECHNICAL FIELD

The disclosure relates to the on-site generation of energy (e.g., electrical power or heat) in a multi-unit building.

BACKGROUND

A building (e.g., a residential or commercial building) can be constructed to accommodate multiple different occupants. For instance, a building can be constructed such that it includes multiple different units or sections, where each unit or section is designed to accommodate one or more occupants.

As an example, a residential building can include multiple different residential units. Each individual residential unit can include one or more bedrooms, living rooms, dining rooms, kitchens, bathrooms, and/or other spaces for a person or group of people to dwell. Example multi-unit residential buildings include apartments and condominiums.

As another example, a commercial building can include multiple different commercial units. Each individual commercial unit can include one or more offices, storage rooms, retail spaces, manufacturing spaces, bathrooms, kitchens, and/or other spaces. Example multi-unit commercial buildings include office buildings and shopping centers.

Multi-unit buildings are often powered using electrical power received from an external source (e.g., a municipal or public power grid). As an example, a multi-unit building can receive electrical power from an external source, and distribute the electrical power to one or more of its units for use.

Waste produced by the occupants of a multi-unit building can be removed in various ways. As an example, biological waste (e.g., urine, fecal matter, food waste, etc.) can be removed using a sewer line extending from the multi-unit building to an external sewer system (e.g., a municipal or public sewer system). As another example, waste can be manually collected (e.g., using a garbage collection container), and manually removed from the multi-unit buildings.

SUMMARY

Implementations for generating electrical power on-site a multi-unit building are described herein.

In general, in an aspect, a system includes an anaerobic digestion tank, a gas storage tank in fluid communication with the anaerobic digestion tank, a power generator in fluid communication with the gas storage tank, a power distribution system in communication with the power generator, and an electronic control system in communication with the anaerobic digestion tank, the gas storage tank, power generator, and the power distribution system. The anaerobic digestion tank is configured to receive biological waste from a sewer line of a multi-unit building, and allow the received biological waste to be digested to produce a combustible gas. The gas storage tank is configured to receive the combustible gas from the anaerobic digestion tank, and store the combustible gas. The power generator is configured to receive the combustible gas from the gas storage tank, and combust the combustible gas to produce at least one of electrical power or heat. The power distribution system is configured to receive the electrical power from the power generator, store at least some of the electrical power in one or more batteries, and distribute at least some of the stored electrical power to one or more electrical devices in the multi-unit building. The electronic control system is configured to control an operation of each of the anaerobic digestion tank, the gas storage tank, the power generator, and the power distribution system.

Implementations of this aspect can include one or more of the following features.

In some implementations, the system can disposed within the multi-unit building.

In some implementations, the combustible gas can include methane.

In some implementations, the combustible gas can be predominantly methane.

In some implementations, the sewer line of the multi-unit building can be a pre-existing conduit in the multi-building configured to receive the biological waste from at least one toilet in the building. The anaerobic digestion tank can be configured to receive biological waste from the sewer line through a relay conduit extending between the sewer line and the anaerobic digestion tank.

In some implementations, the biological waste can include a solid portion and a liquid portion. The anaerobic digestion tank can include a first outlet valve configured to separate at least some of the liquid portion from the solid portion, and direct at least some of the liquid portion to a first waste conduit for removal from the multi-unit building.

In some implementations, anaerobic digestion tank can include a second outlet valve configured to direct at least some of the solid portion to a second waste conduit for removal from the system.

In some implementations, the anaerobic digestion tank can include a mass sensor configured to determine a mass of the biological waste contained within the anaerobic digestion tank. The system can further include a transmitter configured to transmit a notification message to a remote device when the mass of the biological waste contained within the anaerobic digestion tank exceeds a threshold mass.

In some implementations, the anaerobic digestion tank can include a first pressure sensor configured to determine a first pressure within the anaerobic digestion tank. The system can further include a first pump configured to direct the combustible gas from the anaerobic digestion tank to the gas storage tank when the first pressure exceeds a first threshold pressure.

In some implementations, the gas storage tank can include a second pressure sensor configured to determine a second pressure within the gas storage tank. The system can further include a second pump configured to direct the combustible gas from the gas storage tank to the power generator when the second pressure exceeds a second threshold pressure.

In some implementations, the electronic control system can be configured to receive a first input from a user specifying the first threshold pressure, and operate the first pump to direct the combustible gas from the anaerobic digestion tank to the gas storage tank when the first pressure exceeds a first threshold pressure.

In some implementations, the electronic control system can be configured to receive a second input from the user specifying the second threshold pressure, and operate the second pump to direct the combustible gas from the gas storage tank to the power generator when the second pressure exceeds the second threshold pressure.

In some implementations, the second pressure can be greater than the first pressure.

In some implementations, the system can further include a moisture filter configured to remove moisture from the combustible gas as the combustible gas is directed from the anaerobic digestion tank to the gas storage tank.

In some implementations, the power distribution system can be further configured to receive external electrical power from a power source external to the multi-unit building, determine an amount of electrical power stored by the one or more batteries, and upon determining that the amount of electrical power stored by the one or more batteries is less than a threshold amount of electrical power, distributing at least some of the received external electrical power to one or more electrical devices in the multi-unit building.

In some implementations, the power source can be external to the multi-unit building is an external power grid.

In some implementations, the electronic control system can be configured to receive an input from a user specifying the threshold amount of electrical power, and operate the power distribution system to distribute at least some of the received external electrical power to the one or more electrical devices in the multi-unit building when the amount of electrical power stored by the one or more batteries is less than the threshold amount of electrical power.

In some implementations, the power distribution system can be further configured to receive external electrical power from a power source external to the multi-unit building, determine, for each unit of the multi-unit building, a respective amount of electrical power consumed by the unit over a period of time, and upon determining that the amount of electrical power consumed by a particular unit over the period of time exceeds a threshold amount of electrical power, distributing at least some of the received external electrical power to one or more electrical devices in that unit.

In some implementations, the electronic control system can be configured to receive an input from a user specifying the threshold amount of electrical power, and operate the power distribution system to distribute at least some of the received external electrical power to one or more electrical devices in a particular unit when the amount of electrical power consumed by that unit over the period of time exceeds the threshold amount of electrical power.

In some implementations, the system can further include a photovoltaic power generator including one or more photovoltaic modules. The photovoltaic power generator can be configured to generate additional electrical power using light energy incident upon the one or more photovoltaic modules. The power distribution system can be further configured to receive the additional electrical power from the photovoltaic power generator, store at least some of the additional electrical power in the one or more batteries, and distribute at least some of the stored additional electrical power to one or more electrical devices in the multi-unit building.

In some implementations, the system can further include an environmental regulation system configured to distribute at least some of the heat generated by the power generator to one or more units of the multi-unit building.

In some implementations, the system can further include a water distribution system configured to receive at least some of the heat generated by the power generator, heat water using the received heat, and distribute the heated water to one or more units of the multi-unit building.

In some implementations, the anaerobic digestion tank can include a heating element configured to apply heat to the anaerobic digestion tank. The electronic control system can be in communication with the heating element and can be configured to regulate a temperature of the anaerobic digestion tank using the heating element.

In some implementations, the anaerobic digestion tank can include an inlet valve. The anaerobic digestion tank can be configured to receive a digestion-accelerating agent through the inlet valve.

In some implementations, the anaerobic digestion tank can be further configured to receive additional biological waste from a garbage conduit of a multi-unit building, and allow the received additional biological waste to be digested to produce the combustible gas.

In another aspect, a method includes receiving, in an anaerobic digestion tank, biological waste from a sewer line of a multi-unit building; allowing the received biological waste to be digested in the anaerobic digestion tank to produce a combustible gas; directing the combustible gas from the anaerobic digestion tank to a gas storage tank; directing the combustible gas from the gas storage tank to a power generator; combusting the combustible gas using the power generator to produce at least one of electrical power or heat; directing the electrical power from the power generator to a power distribution system; storing, by the power distribution system, at least some of the electrical power in one or more batteries; and distributing, by the power distribution system, at least some of the stored electrical power to one or more electrical devices in the multi-unit building.

Implementations of this aspect can include one or more of the following features.

In some implementations, the combustible gas can include methane.

In some implementations, the combustible gas can be predominantly methane.

In some implementations, the method can further include disposing the anaerobic digestion tank, the gas storage tank, the power generator, and the power distribution system within the multi-unit building.

In some implementations, the sewer line of the multi-unit building can be a pre-existing conduit in the multi-building configured to receive the biological waste from at least one toilet in the building. The method can include installing a relay conduit extending between the sewer line and the anaerobic digestion tank to divert the biological waste from the sewer line to the anaerobic digestion tank.

In some implementations, the biological waste can include a solid portion and a liquid portion. The method can further include separating, by a first outlet valve of the anaerobic digestion tank, at least some of the liquid portion from the solid portion, and directing, by the first outlet valve of the anaerobic digestion tank, at least some of the liquid portion to a first waste conduit for removal from the multi-unit building.

In some implementations, the method can further include directing, by a second outlet valve, at least some of the solid portion to a second waste conduit for removal from the anaerobic digestion tank.

In some implementations, the method can further include determining, using a mass sensor, a mass of the biological waste contained within the anaerobic digestion tank, and transmitting, using a transmitter, a notification message to a remote device when the mass of the biological waste contained within the anaerobic digestion tank exceeds a threshold mass.

In some implementations, the method can further include determining, using a first pressure sensor, a first pressure within the anaerobic digestion tank, and directing, using a first pump, the combustible gas from the anaerobic digestion tank to the gas storage tank when the first pressure exceeds a first threshold pressure.

In some implementations, the method can further include determining, using a second pressure sensor, a second pressure within the gas storage tank, and directing, using a second pump, the combustible gas from the gas storage tank to the power generator when the second pressure exceeds a second threshold pressure.

In some implementations, the method can further include receiving, at an electronic control system, a first input from a user specifying the first threshold pressure, and operating, by the electronic control system, the first pump to direct the combustible gas from the anaerobic digestion tank to the gas storage tank when the first pressure exceeds a first threshold pressure.

In some implementations, the method can further include receiving, at the electronic control system, a second input from the user specifying the second threshold pressure, and operating, by the electronic control system, the second pump to direct the combustible gas from the gas storage tank to the power generator when the second pressure exceeds the second threshold pressure.

In some implementations, the second pressure can be greater than the first pressure.

In some implementations, the method can further include removing, by a moisture filter, moisture from the combustible gas as the combustible gas is directed from the anaerobic digestion tank to the gas storage tank.

In some implementations, the method can further include receiving, at the power distribution system, external electrical power from a power source external to the multi-unit building; determining an amount of electrical power stored by the one or more batteries; and upon determining that the amount of electrical power stored by the one or more batteries is less than a threshold amount of electrical power, distributing at least some of the received external electrical power to one or more electrical devices in the multi-unit building.

In some implementations, the power source external to the multi-unit building can be an external power grid.

In some implementations, the method can further include receiving, at the electronic control system, an input from a user specifying the threshold amount of electrical power, and operating, by the electronic control system, the power distribution system to distribute at least some of the received external electrical power to one or more electrical devices in the multi-unit building when the amount of electrical power stored by the one or more batteries is less than the threshold amount of electrical power.

In some implementations, the method can further include receiving, at the power distribution system, external electrical power from a power source external to the multi-unit building; determining, for each unit of the multi-unit building, a respective amount of electrical power consumed by the unit over a period of time; and upon determining that the amount of electrical power consumed by a particular unit exceeds a threshold amount of electrical power, distributing at least some of the received external electrical power to one or more electrical devices in that unit.

In some implementations, the method can further include receiving, at the electronic control system, an input from a user specifying the threshold amount of electrical power, and operating, by the electronic control system, the power distribution system to distribute at least some of the received external electrical power to one or more electrical devices in the particular unit when the amount of electrical power consumed by that unit over the period of time exceeds the threshold amount of electrical power.

In some implementations, the method can further include generating, using a photovoltaic power generator, additional electrical power using light energy incident upon one or more photovoltaic modules of the photovoltaic power generator; directing the additional electrical power from the photovoltaic power generator to a power distribution system; storing at least some of the additional electrical power in the one or more batteries; and distributing at least some of the stored additional electrical power to one or more electrical devices in the multi-unit building.

In some implementations, the method can further include distributing, using an environmental regulation system, at least some of the heat generated by the power generator to one or more units of the multi-unit building.

In some implementations, the method can further include receiving, using a water distribution system, at least some of the heat generated by the power generator; heating, using the water distribution system, water using the received heat; and distributing, using the water distribution system, the heated water to one or more units of the multi-unit building.

In some implementations, the method can further include regulating, using an electronic control system, a temperature of the anaerobic digestion tank using a heating element of the anaerobic digestion tank. The heating element can be configured to apply heat to the anaerobic digestion tank.

In some implementations, the method can further include receiving, by an inlet element of the anaerobic digestion tank, a digestion-accelerating agent into the anaerobic digestion tank.

In some implementations, the further can further include receiving, in the anaerobic digestion tank, additional biological waste from a garbage conduit of a multi-unit building, and allowing the received additional biological waste to be digested in the anaerobic digestion tank to produce the combustible gas.

The details of one or more embodiments are set forth in the accompanying drawings and the description below. Other features and advantages will be apparent from the description and drawings, and from the claims.

DETAILED DESCRIPTION

Figure 1:
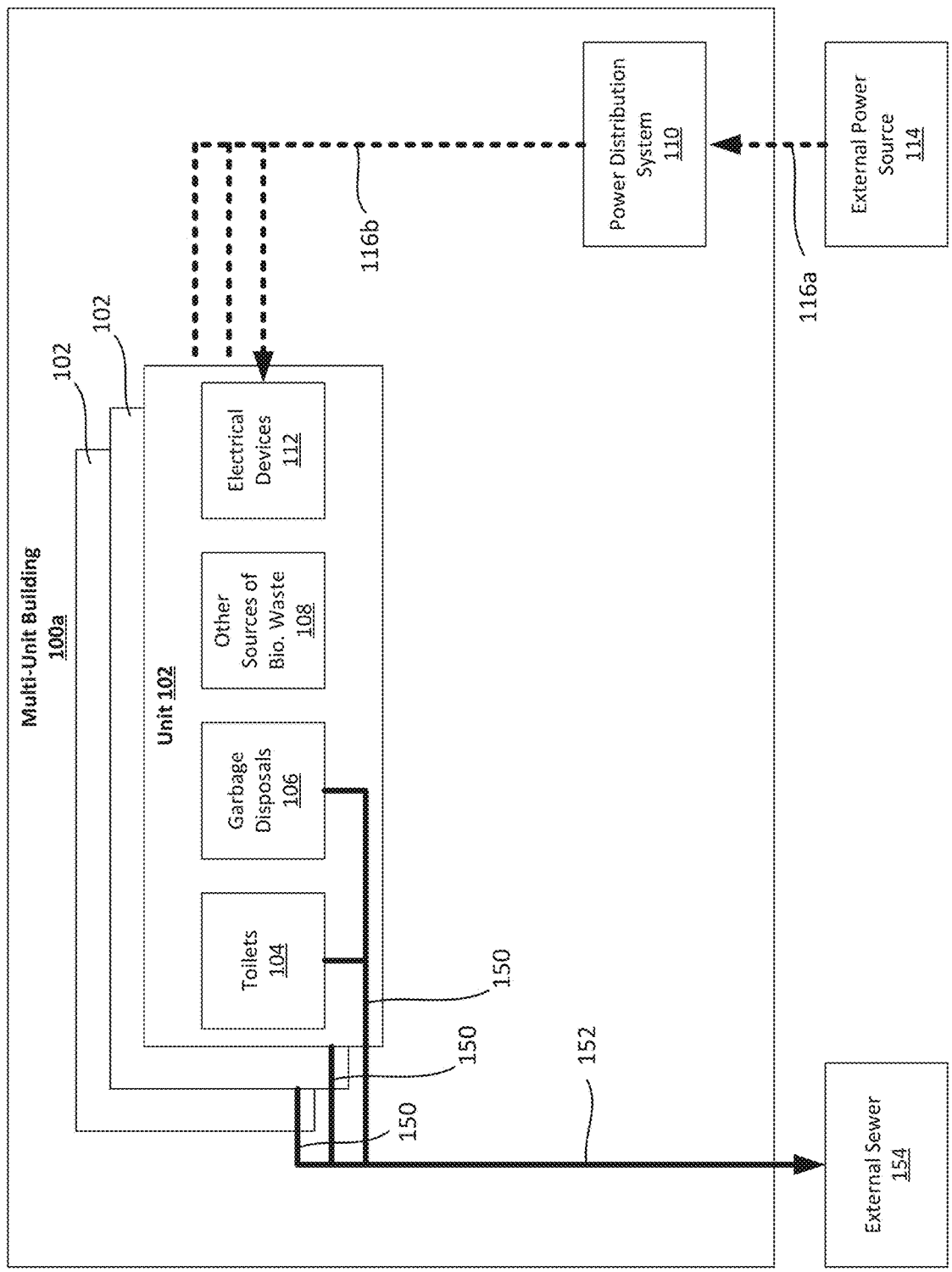
FIG. 1 is a diagram of an example multi-unit building.

An example multi-unit building 100*a* is shown in FIG. 1. The multi-unit building 100*a* can be an enclosed or partially enclosed structure. For example, the multi-unit building 100a can include one or more walls or roofs that enclose or partially enclose one or more interior areas. Further, the multi-unit building 100a can include one or more passageways to provide access to the interior areas. For example, the multi-unit building 100a can include one or more doors, openings, hallways, or other passageways that enable people, animals, or other entities to enter into, move around in, and/or exit from the multi-unit building 100a. Further, the multi-unit building 100a can include one or more openings (e.g., windows, skylights, etc.) that enable light to enter into the building In some cases, the multi-unit building 100a can be constructed in an urban environment (e.g., an environment having a relatively dense concentration of buildings and other infrastructure). In some cases, the multi-unit building 100a can be constructed in a rural or sub-urban environment (e.g., an environment having a relatively less dense concentration of buildings and other infrastructure).

In some cases (e.g., in an urban environment), the multi-unit building 100a can be in close proximity with one or more buildings and/or infrastructure and have a relatively limited "footprint." As an example, the multi-unit building 100a can be abut or nearly abut one or more other buildings and/or infrastructure. In some cases, this can limit the ability to expand or modify the multi-unit building 100a (e.g., due to a relatively small amount of available space surrounding the multi-unit building 100a).

In some cases, the multi-unit building 100a can be a residential building, such as an apartment or a condominium. A residential building can be, for example, a building designed or intended to accommodate one or more inhabitants. For instance, each of the units 102 can be a residential unit. Each residential unit can include one or more bedrooms, living rooms, dining rooms, kitchens, bathrooms, and/or other spaces for a person or group of people to dwell.

In some cases, the multi-unit building 100a can be a commercial building, such as an office building or a shopping center. A commercial building can be, for example, a building designed or intended to facilitate the performance of business-related activities. For instance, each of the units 102 can be a commercial unit. Each residential unit can include one or more offices, storage rooms, retail spaces, manufacturing spaces, bathrooms, kitchens, and/or other spaces that enable its occupants to conduct business-related activities.

In some cases, the multi-unit building 100a can be a "mixed use" building. For example, the multi-unit building 100a can include one or more residential units and one or more commercial units to serve both residential and commercial functions.

In general, each unit 102 can include one or more amenities for the comfort and convenience of the occupants of the unit 102. For example, a unit 102 can include one or more toilets 104 into which a person can urinate or defecate. The one or more toilets 104 can be in fluid communication with a fluid conduit 150 (e.g., one or more pipes), which in turn is in fluid communication with a sewer line 152. Biological waste from the toilets 104 (e.g., urine, feces, etc.) can be removed from the unit 102 and out of the multi-unit building 100a by directing the biological waste from the toilets 104 into the fluid conduit 150, through the sewer line 152, and out of the building into an external sewer 154 (e.g., a municipal or public sewer system). This can be convenient, for example, as it enables the occupants of the multi-unit building 100a to relieve themselves and dispose of the waste in a sanitary manner, without requiring them to leaving the multi-unit building 100a.

As another example, a unit 102 can include one or more garbage disposal systems 106. Garbage disposal systems 106, for example, can be used to physically break down certain forms of biological waste (e.g., crush or grind food waste), such that the waste can be disposed of in a sink or drain. The garbage disposal systems 106 also can be in fluid communication with the fluid conduit 150. Accordingly, biological waste from the garbage disposal systems 106 (e.g., food waste) can be removed from the unit 102 and out of the multi-unit building 100a by directing the biological waste from the garbage disposal systems 106 into the fluid conduit 150, through the sewer line 152, and out of the building into an external sewer 154. This can be convenient, for example, as it enables the occupants of the multi-unit building 100a to dispose of certain types of biological waste in a sanitary manner, without requiring them to leaving the multi-unit building 100a.

As another example, a unit 102 can include one or more other sources of biological waste 108. These sources 108 can include, for example, one or more refuse receptacles for collecting biological waste, composting systems, garbage conduits or chutes for collecting biological waste, and so forth. In some cases, the biological waste from the sources 108 must be manually removed from the unit 102 and the multi-unit building 100a by its occupants. For example, in some cases, the biological waste contained within the sources 108 may be unsuitable for disposal by the toilets 104 and/or the garbage disposal system 106 (e.g., too sturdy, too bulky, etc., to be disposed in this manner).

In some cases, the multi-unit building 100a can include multiple different fluid conduits 150 (e.g., a separate fluid conduit 150 for each unit 102), each feeding into a common sewer line 152. This can be beneficial, for example, as it enables biological waste to be collected and removed from the multi-unit building 100a via a single connection point to the external sewer 154 (e.g., rather than multiple individual connections to the external sewer 154). This can reduce the cost of implementing the multi-unit building 100a and/or improve the reliability of the multi-unit building (e.g., by reducing the number of components that need to be installed and/or serviced).

Further, the multi-unit building 100a can include a power distribution system 110 to distribute electrical power to one or more electrical devices 112 in each of the units 102. For example, the power distribution system 110 can receive electrical power from an external power source 114 (e.g., a municipal power grid or public power grid) through an electrical conduit 116a, and selectively distribute the received electrical power to the units 102 via electrical conduits 116b for use by the electrical devices 112. Electrical devices 112 can include, for example, lights, appliances, electronic devices, or any other device that operates using electrical power.

In the example shown in FIG. 1, the multi-unit building 100a relies upon the external sewer system 154 for the disposal of biological waste. Further, the multi-unit building 100a relies upon the external power source 114 for electrical power. In some cases, this may be convenient, as it delegates the responsibility of disposing of biological waste and/or providing electrical power to one or more third parties (e.g., municipal authorities, public works organizations, or other entities). However, in some cases, this may be relatively expensive, as such third parties often require fees for their services. Further, in some cases, this may negatively impact the environment, as biological waste is merely removed from the multi-unit building 100a without reclamation. Further, the multi-unit building 100a is not self-sustaining with respect to electrical power, and requires that electrical power be constantly supplied from a third party for use by its occupants.

Figure 2:
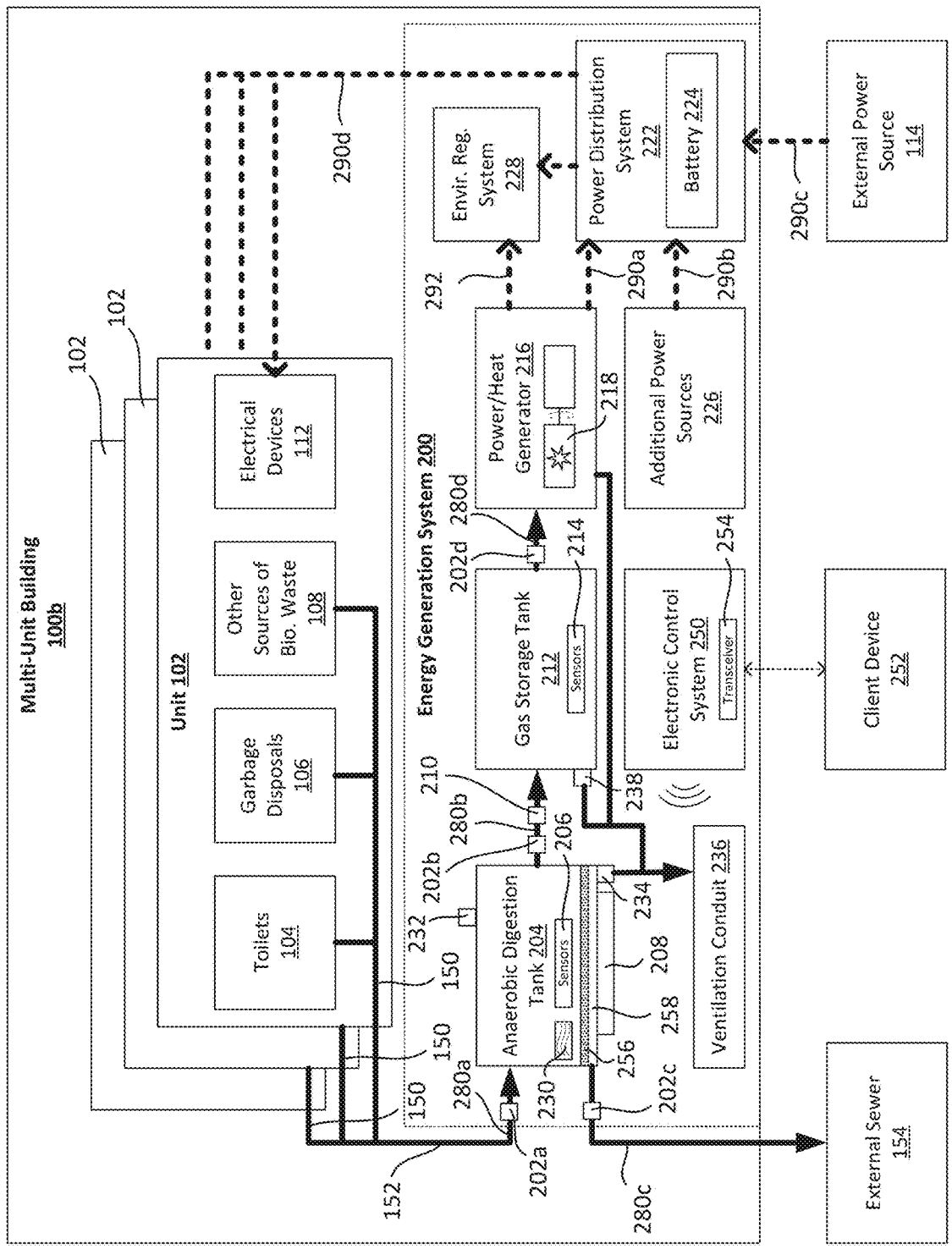
FIG. 2 is a diagram of an example multi-unit building having a energy generation system described herein.

An example multi-unit building 100b configured for on-site generation of energy (e.g., electrical power and/or heat) is shown in FIG. 2. The multi-unit building 100b is generally similar to the multi-unit building 100a shown in FIG. 1. For example, the multi-unit building 100b can be an enclosed or partially enclosed structure, and can have one or more one or more passageways and openings (e.g., to provide access to its interior areas, to enable light to enter into the building, etc.). The multi-unit building 100b can be a residential, commercial, or "mixed use" building, and can include one or more units 102 (e.g., one or more residential units and/or commercial units). Further, the multi-unit building 100b can also include one or more amenities, such as one or more toilets 104, garbage disposal systems 106, and other sources of biological waste 108.

However, in this example, the multi-unit building 100b does not completely rely on the external sewer 154 to dispose of biological waste, nor does it completely rely on the external power source 114 for electrical power. Instead, the multi-unit building 100b includes an energy generation system 200 for processing biological waste, generating electrical power on-site, storing generated electrical power, and distributing the stored electrical power for use by one or more occupants. For example, the system 200 is configured to collect biological waste, and use the collected biological waste to generate electrical power on-site (e.g., through an anaerobic digestion reaction). Further, the system 200 is also configured to generate additional electrical power using one or more additional power sources. This can include, for example, solar power sources (e.g., photovoltaic panels), wind-based power sources (e.g., wind turbines), kinetic power sources, thermoelectric power sources, and/or other power sources. The generated electrical power can be stored for future use. Further, the system 200 is configured to distribute the generated electrical power to one or more of the units 102 for use (e.g., to power one or more electrical devices 112 in the units 102). Further, the system 200 also can be configured to generate heat on-site using the collected biological waste, and distribute the heat throughout the multi-unit building 100b. In some cases, some or all of the system 200 can be positioned within the multi-unit building 100b and/or positioned along an outer periphery of the multi-unit building 100b.

In some cases, the system 200 reduces the environmental impact of the multi-unit building 100b. For instance, as the system 200 consumes biological waste to generate electrical power and/or heat, the multi-unit building 100b expels less biological waste into external sewer 154. Further, as the system 200 generates electrical power on-site, the multi-unit building 100b consumes less electrical power from the external power source 114. Thus, the negative impact of the multi-unit building 100b on its surrounding environment is reduced, as is the building's demand for external resources.

In some cases, the system 200 can generate electrical power to supplement that received from the external power source 114. For example, the system 200 can generate an amount of electrical power to fulfill a portion of the power demand of the multi-unit building 100b, and use the external power source 114 to fulfill the remaining demand. In some cases, the system 200 can enable the multi-unit building 102b to be substantially self-sustaining with respect to electrical power. For example, the system 200 can generate a sufficient amount of electrical power to meet substantially the entire demand of the multi-unit building 100b without relying on the external power source 114.

In some cases, the system 200 can be incorporated into the multi-unit building 100b during the initial construction of the multi-unit building 100b. This can be beneficial, for example, as it enables a multi-unit building 100b to operate in a more efficient and environmentally friendly manner immediately upon completion.

In some cases, the system 200 can be incorporated into the multi-unit building 100b after the construction of the multi-unit building 100b. For example, sometime after the multi-unit building 100b has been constructed, the multi-unit building 100b can be modified or retrofitted to incorporate the system 200. This can be beneficial, for example, as it enables the owners or operators of pre-existing buildings to improve the operation of their buildings, even after the building has already been constructed.

The functionality of the system 200 is described in greater detail below.

In a similar manner as described with respect to FIG. 1, the toilets 104 and the garbage disposal systems 106 can be in fluid communication with one or more fluid conduits 150, which are turn in fluid communication with a sewer line 152. Further, the other sources of biological waste 108 also can be in fluid communication with the one or more fluid conduits 150. Biological waste from the toilets 104, the garbage disposal system 106, and the sources 108 can be removed from each of the units 102 by directing the biological waste into the fluid conduit 150, and into the sewer line 152.

The sewer line 152 directs the biological waste into the system 200 through a fluid conduit 280a and a flow regulation device 202a (which can include one or more pumps and/or valves). The flow regulation device 202a is configured to regulate the flow of biological waste into the system 200 (e.g., by selectively opening or closing one or more vales to control the rate of flow of biological waste through it, and/or operating one or more pumps to convey biological waste).

Biological waste from the sewer line 152 passes through the flow regulation device 202a and into an anaerobic digestion tank 204. The anaerobic digestion tank 204 is configured convert the biological waste into a combustible gas through an anaerobic digestion process. In an example process, the anaerobic digestion tank 204 incudes a reservoir, within which the biological waste is deposited. Further, microorganisms capable of digesting biological materials in an anaerobic environment are also deposited into the reservoir. Example microorganisms include acetic acid-forming bacteria (e.g., acetogens, which generate acetate as a product of anaerobic respiration) and methane-forming archaea (e.g., methanogens, which produce methane as a metabolic byproduct in anoxic conditions). The biological waste is digested by the microorganisms within the reservoir, producing a combustible gas (e.g., methane). The combustible gas produced within the anaerobic digestion tank 204 is removed by a flow regulation device 202b through a fluid conduit 280b.

In some cases, the anaerobic digestion process can be described by the chemical reaction below, where organic material such as glucose is biochemically digested into carbon dioxide ($CO_2$) and methane ($CH_4$) by the anaerobic microorganisms.

$$C_6H_{12}O_6 \rightarrow 3CO_2 + 3CH_4$$

This process can be performed according to multiple difference stages, including hydrolysis, acidogenesis, acetogenesis, and methanogenesis.

Hydrolysis—In many cases, biological waste is made up of large organic polymers. For the microorganisms in anaerobic digestion tank 204 to access the energy potential of the material, these chains can first be broken down into their smaller constituent parts. These constituent parts, or monomers, such as sugars, are readily available to other microorganisms. The process of breaking these chains and dissolving the smaller molecules into solution is called hydrolysis. Through hydrolysis, the complex organic molecules are broken down into simple sugars, amino acids, and fatty acids.

Acetate and hydrogen produced in the first stages can be used directly by methanogens. Other molecules, such as volatile fatty acids (VFAs) with a chain length greater than that of acetate can be first be catabolised into compounds that can be directly used by methanogens.

Acidogenesis—The biological process of acidogenesis results in further breakdown of the remaining components by acidogenic (fermentative) bacteria. Here, VFAs are created, along with ammonia, carbon dioxide, and hydrogen sulfide, as well as other byproducts.

Acetogenesis—The third stage of anaerobic digestion is acetogenesis. Here, simple molecules created through the acidogenesis phase are further digested by acetogens to produce largely acetic acid, as well as carbon dioxide and hydrogen.

Methanogenesis—The terminal stage of anaerobic digestion is the biological process of methanogenesis. Here, methanogens use the intermediate products of the preceding stages and convert them into methane, carbon dioxide, and water. These components make up the majority of the biogas emitted from the system. The remaining, indigestible material the microbes cannot use and any dead bacterial remains constitute the digestate.

In some cases, the biological waste includes both solid components and liquid components. In some cases, some or all of the liquid components can be removed from the anaerobic digestion tank 204 through a fluid conduit 280c and a flow regulation device 202c. For example, the anaerobic digestion tank 204 can include one or more filters 256 (e.g., gravity driven synthetic or organic filters, such as filters having clay pebbles encased in netting) separating an upper portion of the anaerobic digestion tank 204 from a drainage channel 258 extending along a bottom of the anaerobic digestion tank 204. The filters 256 allow some or all of the liquid components to pass into the drainage channel 258, while retaining the solid components in the upper portion of the anaerobic digestion tank 204. This drainage channel 258 can be in fluid communication with the fluid conduit 280c and the flow regulation device 202c, such that the separated liquid components are directed out of the anaerobic digestion tank 204. In some cases, the filters 256 can also partially or fully neutralize or decontaminate the separated liquid components (e.g., by removing ammonia or other toxic substances). This can be useful, for example, as it enables the solid components to remain in the anaerobic digestion tank 204 (e.g., such that they are digested), while removing at least some of the liquid components (e.g., which may contribute less to the digestion process). Further, as the filters 256 are gravity fed, they can be operated very efficiently (e.g., consuming little to no electrical power). The fluid conduit 280c can be in fluid communication with the external sewer system 154, such that the liquid components are removed from the multi-unit building 100b.

In some cases, the fluid conduit 280c can be in fluid communication with a water purification system. The water purification system can receive the liquid components (e.g., "dark" or "brown" water) from the anaerobic digestion tank 204, and treat the liquid components (e.g., by removing contaminants, particles, or other substances) to obtain usable water (e.g., potable water and/or water for non-consumption purposes, such water used for toilets, irrigation, etc.). In some cases, some or all of the purified water can be directed to the external sewer 154. In some cases, some or all of the purified water can be retained on-site the multi-unit building 100b (e.g., for use by the occupants of the multi-unit building 100b).

In some cases, the flow regulation devices 202a-c can be controlled by an electronic control system 250 based on measurements provided by one or more sensors 206. For example, the sensors 206 can include one or more pressure sensors configured to monitor the pressure within the anaerobic digestion tank 204. The sensors 206 transmit the pressure measurements to the electronic control system 250 (e.g., via one or more transceivers). Based on these measurements, the electronic control system 250 regulates the pressure within the anaerobic digestion tank 204. For example, if the pressure is particularly high (e.g., above a particular threshold pressure), the electronic control system 250 can operate the flow regulation device 202a to prevent additional biological waste from being passed into the anaerobic digestion tank 204 (e.g., by closing one or more valves and/or deactivating one or more pumps). As another example, the electronic control system 250 can operate the flow regulation device 202b, and/or the flow regulation device 202c to remove combustible gas and/or liquid from the anaerobic digestion tank 204 (e.g., by opening one or more valves and/or activating one or more pumps).

In some cases, if the mass is particularly high (e.g., above a particular alarm threshold pressure), the electronic control system 250 can transmit a notification (e.g., a text message, chat message, e-mail, fax message, telephone call, or any other form of communication) to a client device 252 using a transceiver 254, notifying a user of the client device 252 that the pressure within the anaerobic digestion tank 204 is at dangerous, unsafe, or undesirable levels. The pressure within the anaerobic digestion tank 204 can be relieved via a safety or emergency valve 234. In some cases, the safety or emergency valve 234 can be in gaseous communication with a ventilation system 236 (e.g., an air riser that extends to a top of the building 100b) to prevent contamination of the building and/or to expel noxious or otherwise unpleasant odors from the building 100b.

As another example, the sensors 206 can include one or more mass sensors to monitor the mass of solid components within the anaerobic digestion tank 204. The sensors 206 transmit the mass measurements to the electronic control system 250 (e.g., via one or more transceivers). These measurements can be used to determine when the anaerobic digestion tank 204 is filling up with digestate (e.g., indigestible material), and should be emptied. For example, if the mass is particularly high (e.g., above a particular threshold mass), the electronic control system 250 can transmit a notification (e.g., a text message, chat message, e-mail, fax message, telephone call, or any other form of communication) to a client device 252 using a transceiver 254, notifying a user of the client device 252 that digestate should be removed from the anaerobic digestion tank 204. The anaerobic digestion tank 204 can include an access port 208 (e.g., a valve, a drain, a channel, a door, a panel, or other port) to facilitate removal of the digestate from the anaerobic digestion tank 204. In some cases, the removed digestate can be used as compost, mulch, or other purposes.

In some cases, the threshold pressure, the alarm threshold pressure, and/or the threshold mass can be user-configurable values. For example, the user can input a particular threshold pressure, alarm threshold pressure, and/or a particular threshold mass into the electronic control system 250 (e.g., using a user interface provided by the electronic control system 250, such as a control panel or a computerized user interface). In response, the electronic control system 250 can record the received values, and operate in accordance with those values.

The anaerobic digestion tank 204 can be pressurized during operation. Further, the anaerobic digestion tank 204 can be configured such that substances can be removed from within the anaerobic digestion tank 204 without completely depressurizing the anaerobic digestion tank 204. For example, the access port 208 can be configured such that disgestate can be removed without completely depressurizing the anaerobic digestion tank 204 (e.g., through the use of a pressurized "desludging" valve coupled to a collection tube or hose). As another example, the flow regulation device 202b can include a pressurized valve, such that combustible gas can be removed without completely depressurizing the anaerobic digestion tank 204.

Further, the anaerobic digestion tank 204 can be configured such that additional substances can introduced into the anaerobic digestion tank 204 without completely depressurizing the anaerobic digestion tank 204. For example, the anaerobic digestion tank 204 can include a pressurized inlet valve 232 configured such that materials (e.g., digestion-acceleration agents, such as glycol) can be introduced into the anaerobic digestion tank 204 without completely depressurizing the anaerobic digestion tank 204. Further, the flow regulation device 202b also can include a pressurized valve, such that biological waste can be introduced into the anaerobic digestion tank 204 without completely depressurizing the anaerobic digestion tank 204

In some cases, the anaerobic digestion tank 204 can include a heating element 230 (e.g., a heating coil) to regulate a temperature within the anaerobic digestion tank 204. This can be useful, for example, as the anaerobic digestion process may be most efficient at particular temperatures or temperature ranges.

In some cases, the sensors 206 can include one or more temperature sensors to monitor the temperature within the anaerobic digestion tank 204. The sensors 206 transmit the temperature measurements to the electronic control system 250 (e.g., via one or more transceivers). In response, the electronic control system 250 can control the operation of the heating element 230 (e.g., selectively turning on or off the heating element 230) to regulate the temperature. For example, if the temperature is particularly low (e.g., below a particular threshold temperature), the electronic control system 250 can activate the heating element 230.

In some cases, the threshold temperature also can be a user-configurable value. For example, the user can input a particular threshold temperature into the electronic control system 250 (e.g., using a user interface provided by the electronic control system 250, such as a control panel or a computerized user interface). In response, the electronic control system 250 can record the received value, and operate in accordance with that value.

In some cases, the sensors 206 can include one or more sensors configured to monitor the composition of gas within the anaerobic digestion tank 204. The sensors 206 can transmit the composition measurements to the electronic control system 250 (e.g., via one or more transceivers). In response, the electronic control system 250 can control the operation of the energy generation system 200. For example, the electronic control system 250 can notify a user and/or selectively discontinue operation of the system if unexpected, undesirable, and/or dangerous gases are found (e.g., a high concentration of sulfide gas, potentially indicative of corrosion within the anaerobic digestion tank 204). As another example, the electronic control system 250 can notify a user of the composition of gas within the anaerobic digestion tank 204 (e.g., for safety, research, and/or academic purposes).

In some cases, the anaerobic digestion tank 204 can be configured to stir, agitate, or otherwise mix the contents of the anaerobic digestion tank 204. As an example, the anaerobic digestion tank 204 can include one or more agitators, stirrers, impellers, mixers, or other such devices. This can be beneficial, for example, to facilitate digestion within the anaerobic digestion tank 204.

Combustible gas is removed from the anaerobic digestion tank 204 by a flow regulation device 202b through a fluid conduit 280b, and passed through one or more filters 210. The filters 210 remove moisture and/or other contaminants (e.g., substances other than the combustible gas) to improve the purity of the combustible gas. In some case, different filters 210 can be configured to remove different substances from the combustible gas (e.g., one or more filters can be used to remove moisture, one or more other filters can be used to remove ammonia, etc.).

The filtered combustible gas is directed into a gas storage tank 212. The gas storage tank 212 is configured to store the combustible gas under pressure. For example, in some cases, the pressure of the combustible gas within the gas storage tank 212 can be higher than the pressure within the anaerobic digestion tank 204. This can be beneficial, for example, as it enables the gas storage tank 212 to store a relatively larger amount of combustible gas, and under conditions that might otherwise be detrimental to the anaerobic digestion process.

In some cases, the flow regulation device 202b also can be controlled by the electronic control system 250 based on measurements provided by one or more sensors 214. For example, the sensors 214 can include one or more pressure sensors configured to monitor the pressure within the gas storage tank 212. The sensors 206 transmit the pressure measurements to the electronic control system 250 (e.g., via one or more transceivers). Based on these measurements, the electronic control system regulates the pressure within the gas storage tank 212. For example, if the pressure is particularly high (e.g., above a particular threshold pressure, corresponding to a safe limit of the gas storage tank 212), the electronic control system 250 can operate the flow regulation device 202b to prevent additional combustible gas from being passed into the gas storage tank 212 (e.g., by closing one or more valves and/or deactivating one or more pumps).

Further, the electronic control system 250 can also transmit notifications to one or more users. For example, if the pressure in the gas storage tank 212 is particularly high (e.g., above another threshold pressure, corresponding to a "warning" or abnormally high pressure), the electronic control system 250 can transmit a notification (e.g., a text message, chat message, e-mail, fax message, telephone call, or any other form of communication) to the client device 252 using a transceiver 254, notifying a user of the client device 252 that gas storage tank 212 may have an abnormally high pressure. The pressure within the gas storage tank 212 can be relieved via a safety or emergency valve 238 (e.g., automatically by the electronic control system 250, or manually by a user). In some cases, the safety or emergency valve 238 can be in gaseous communication with the ventilation system 236 (e.g., an air riser that extends to a top of the building 100b) to prevent contamination of the building and/or to expel noxious or otherwise unpleasant odors from the building 100b. In some cases, the "warning" threshold pressure can be lower than the safety limits of the gas storage tank 212 (e.g., the maximum storage capacity of the gas storage tank 212), such that users are notified before there is a potentially dangerous situation and have sufficient time to take appropriate action.

In some cases, these threshold pressures also can be a user-configurable value. For example, the user can input particular threshold pressures into the electronic control system 250 (e.g., using a user interface provided by the electronic control system 250, such as a control panel or a computerized user interface). In response, the electronic control system 250 can record the received value, and operate in accordance with that value.

The combustible gas stored within the gas storage tank 212 is selectively dispensed by a regulation device 202d through a fluid conduit 280d to the power/heat generator 216 (e.g., to provide fuel to generate power and/or heat).

The power/heat generator 216 combusts the combustible gas to generate power and/or heat. As an example, the power/heat generator 216 can ignite the combustible gas to drive a combustion engine 218. Mechanical energy produced by the combustion engine 218 can be converted into electrical power using an electric generator 220. As another example, the power/heat generator 216 can ignite the combustible gas, and collect the heat that is produced as the combustible gas burns (e.g., using a heat exchanger or radiator). As another example, in generating electrical power, the power/heat generator 216 can produce waste heat. The waste heat can be collected (e.g., using a heat exchange or radiator).

In some cases, the power/heating generator 216 can be a combined heat and power (CHP) system (e.g., producing both electrical power and heat). In some cases, the power/heating generator 216 can produce solely power or solely heat.

In some cases, the power/heat generator 216 and the flow regulation device 202d can be controlled by the electronic control system 250. For example, the electronic control system 250 can monitor a demand or electrical power and/or heat by the multi-unit building 102. If the electronic control system 250 determines that electrical power and/or heat is required to satisfy the demand, the electronic control system 250 can activate the pump 202d, such that combustible gas flows from the gas storage tank 212 to the power/heat generator 216. Further, the electronic control system 250 can activate the power/heat generator 216 to produce electric power and/or heat using the combustible gas.

As another example, the electronic control system 250 can monitor the pressure within the gas storage tank 212. If the pressure is above a particular threshold pressure (e.g., corresponding to a minimal amount of pressure needed to drive the power/heat generator 216), the electronic control system 250 can activate the pump 202d (e.g., to provide combustible gas to the power/heat generator 216).

In some cases, this threshold pressure also can be a user-configurable value. For example, the user can input a particular threshold pressure into the electronic control system 250 (e.g., using a user interface provided by the electronic control system 250, such as a control panel or a computerized user interface). In response, the electronic control system 250 can record the received value, and operate in accordance with that value.

In some cases, the power/heat generator 216 can be in gaseous communication with the ventilation system 236 (e.g., an air riser that extends to a top of the building 100b) to prevent exhaust from the power/heat generator 216 from contaminating the building and/or to expel noxious or otherwise unpleasant odors from the building 100b.

Electrical power generated by the power/heat generator 216 is directed through an electrical conduit 290a (e.g., one or more conductive wires) to the power distribution system 222. The power distribution system 222 stores at least some of the electrical power in one or more batteries 224. Batteries can include, for example, rechargeable batteries such as lithium-ion (Li-ion) cells, nickel-cadmium (NiCd) cells, nickel-zinc (NiZn) cells, and nickel metal hydride (NIMH) cells, among others.

The power distribution system 222 can also receive electrical power one or more additional power sources 226. For example, the power distribution system 222 can receive electrical power provided by one or more solar power sources via an electrical conduit 290b. Solar power sources can include, for example, photovoltaic modules or panels (e.g., "solar panels") that use light energy (e.g., photons incident upon the modules or panels) to generate electrical power through the photovoltaic effect. In some cases, the solar power sources can be positioned on an exterior of the multi-unit building 100b (e.g., on the roof, on an exterior wall, etc.) and/or in proximity to the multi-unit building 100b (e.g., on the ground surrounding the multi-unit building 100b) at a location that receives a substantial amount of sunlight. Electrical power produced by the solar power sources is directed to the power distribution system 222. In turn, the power distribution system 222 can store at least some of the electrical power in the batteries 224.

As another example, the power distribution system 222 can receive electrical power provided by one or more other types of additional power sources 226. These can include, for example, wind-based power sources (e.g., wind turbines), kinetic power sources, thermoelectric power sources, and/or other power sources.

In some cases, the power distribution system 222 can also receive electrical power from the external power source 114 (e.g., a municipal or public power grid) through an electrical conduit 290c. In turn, the power distribution system 222 can store at least some of the electrical power in the batteries 224.

The power distribution system 222 can distribute electrical power to each of the units 102 via one or more electrical conduits 290d. In some cases, the power distribution system 222 can store electrical power in the batteries 224, and selectively distribute the stored electrical power in response to demand by one or more of the electrical devices 112. This can be beneficial, for example, as it enables the power distribution system 222 to store excess electrical power during certain periods of time (e.g., when more electrical power is being generated by the power/heat generator 216 and the additional power sources 226 than is currently being demanded by the units 102), and distribute the stored electrical power during other periods of time (e.g., when demand by the units 102 outstrips generation by the power/heat generator 216 and the additional power sources 226). Accordingly, this enables the energy generation system 200 to provide electrical power in a reliable manner under a variety of different circumstances, even despite inconsistent demand for electrical power by the multi-unit building 100b.

In some cases, the power distribution system 222 can directly route electrical power from the power/heat generator 216, the additional power source 226, and/or the external power source 114 directly to the units 112 (e.g., by bypassing the batteries 224). In some cases, the power distribution system 222 can selectively alternate between routing stored electrical power from the batteries 224 to one or more units 102, and directly routing electrical power from the power/heat generator 216, the additional power source 226, and/or the external power 114 to those units 102.

The power distribution system 222 also can be controlled by the electronic control system 250. For example, the electronic control system 250 can monitor electrical power damage from each of the units 102, and operate the power distribution system 222 to meet the demand (e.g., by routing electrical power from the batteries 224, power/heat generator 216, the additional power source 226, and/or the external power source 114).

In some cases, the electronic control system 250 can prioritize distributing electrical power stored within the batteries 224 over distributing electrical power from the external power source 114. For example, electrical power generated by the power/heat generator 216 and the additional power source 226 can be stored in the batteries 224. The electronic control system 250 can monitor the amount of electrical power stored in the battery 224, and distribute the stored electrical power to meet the demand of the multi-unit building 100b. If the amount of stored electrical power is sufficiently low (e.g., below a threshold power level), the electronic control system 250 can distribute power from the external power source 114 (e.g., in addition to or instead of distributing the stored electrical power). This can be useful, for example, as it enables the energy generation system 200 to operate in a self-sufficient manner with respect to electric power to the extent possible under the circumstances, while also enabling the energy generation system 200 to obtain additional power as needed to meet demand. Thus, the energy generation system 200 can efficiently generate and distribute electrical power to the units 102, without any interruption or loss of service even under high demand.

In some cases, the threshold power level also can be a user-configurable value. For example, the user can input a particular threshold power level into the electronic control system 250 (e.g., using a user interface provided by the electronic control system 250, such as a control panel or a computerized user interface). In response, the electronic control system 250 can record the received value, and operate in accordance with that value.

In some cases, the energy generation system 200 can generate and store electrical power in the batteries 224, and allot a particular amount of stored electrical power to each of the units 102 over a particular time period. For example, the electronic control system 250 can allot 100 kWh of stored electrical power to each of the units 102 each month. During the course of the month, the electronic control system 250 can operate the energy generation system 200 to distribute stored electrical power to each of the units 102 in response to demand, and monitor the amount of electrical power that each unit 102 consumes. If a particular unit 102 consumes more than 100 kWh of the stored electrical power during the month, the electronic control system 250 can discontinue distributing stored electrical power to that unit 102, and instead distribute electrical power to that unit 102 directly from the external power source 114 for the remainder of the month. After the month is over, each unit 102 can again be allotted 100 kWh of stored electrical power. This can be useful, for example, as it enables the units 102 to share the electrical power generated by the energy generation system 200 in a more fair, equitable, and/or predictable manner. If a particular unit 102 exceeds his allotment during a particular time period, that unit 102 is switched to electrical power obtained from the external power source 114, while the other units 102 continue using the stored electrical power in the batteries 224.

In some cases, the threshold power level and/or the time period can be user-configurable values. For example, the user can input a particular threshold power level and/or a particular time period into the electronic control system 250 (e.g., using a user interface provided by the electronic control system 250, such as a control panel or a computerized user interface). In response, the electronic control system 250 can record the received values, and operate in accordance with those values.

In some cases, the power distribution system 222 can measure the amount of electrical power from the external power source 114 that is consumed by each unit 102. These measurements can be used, for example, to assess a fee to the occupants of a unit 102 when that unit 102 uses more than the allotted amount of stored electrical power. Measurements can be made, for example, using an electricity meter (e.g., positioned along the electrical conduit 290d or within the power distribution system 222).

In some cases, an operator or administrator of the external power source 114 can provide each unit 102 with an individual electricity meter for measuring the amount of electrical power from the external power source 114 that is consumed by that unit 102. For example, the operator or administrator of a municipal power grid may provide each unit 102 with an individual electricity meter, and use the measurements from the electricity meter to charge the occupants of each unit 102 for the amount of electrical power that is consumed. In these cases, when the power distribution system 222 distributes stored electrical power from the batteries 224 to a unit 102, it can do so in a manner that bypasses the electricity meter (e.g., such that the occupants of that unit 102 are not charged by the operator or administrator of the external power source 114 for this usage). Further, when the power distribution system 222 distributes electrical power from the external power source 114 to a unit 102, it can do so in a manner that passes through the electricity meter (e.g., such that the occupants of that unit 102 are charged by the operator or administrator of the external power source 114 for this usage). Further, the power distribution system 222 can switch between these two different power routing schemes such that the occupants of the units 102 are charged the correct amount for their usage by the operator or administrator of the external power source 114. For example, the power distribution system 222 can include a switch mechanism for each unit 102 that toggles between (i) delivering stored electrical power along an electrical conduit that bypasses the electricity meter, and (ii) delivering electrical power from the external power source 114 along another electrical conduit that passes through the electricity meter.

In some implementations, the electronic control system 250 can be configured to provide incentives to the occupants of the multi-unit building 100b to encourage occupants to use electrical power in a responsible manner. For example, the electronic control system 250 can monitor the amount of electrical power that is produced by the energy generation system 200, compared to the amount of electrical power that is consumed by the occupants of the multi-unit building 100b. In the event of a surplus, the electronic control system 250 can be configured to distribute some or all of the surplus electrical power to the external power source 114 in exchange for a fee (e.g., monetary compensation). Further, the electronic control system 250 can determine an equitable manner in which the fee should be distributed to the occupants of the multi-unit building 100b. For example, the fees can be distributed proportionately to the occupants of each unit 102 based on their contribution to the surplus (e.g., those who consumed more will receive a smaller portion of the fee or none at all, while those who consumed less will receive a larger portion of the fee). This can be beneficial, for example, as it encourages occupants to use electrical power in a responsible manner (e.g., by enabling them to reap tangible rewards for responsible use).

In an example implementation, the energy generation system 200 can be configured to store approximately 450 kWh of electrical energy, and can have a maximum output of approximately 200,000 V during peak demand. Further, the energy generation system 200 can be configured to generate approximately 15,000 kWh to 20,000 kWh of electrical energy per year using biological waste. Further, the energy generation system 200 can be configured to generate approximately 45 kWh to 50 kWh from solar power sources (e.g., solar panels), and approximately 15 kWh to 20 kWh from other types of power sources. In some cases, the electrical power demand per building can be approximately 80,000 kWh to 90,000 kWh per year.

The amount of electrical power generated by the energy generation system 200 can vary depending on the number of occupants in the multi-unit building. As an example, in some cases, an average American consumes approximately 3,770.00 kJ per day. Assuming that the average number of occupants in a unit is 2.5, for 12 units, this amounts to approximately 41,281,500 kJ (or 11,457 kWh) per year for the building, without factoring in energy losses through conversion and transfer.

Although example parameters are described herein, others are also possible, depending on the implementation.

As described herein, in some cases, the power/heat generator 216 can generate heat (e.g., by igniting or burning the combustible gas), and collect the heat that is produced (e.g., using a heat exchanger or radiator). The collected heat can be routed via a heat conduit 292 (e.g., a heat pipe) to an environmental regulation system 228 for distribution throughout the multi-unit building 100b. Example environmental regulation systems 228 include heating, ventilation, and air conditioning (HVAC) systems, water heaters or boilers, or other devices for controlling an environment of the multi-unit building 100b. For instance, the environmental regulation system 228 can use the collected heat to heat air and/or water, and distribute the heated air and/or water to the units 102.

In some cases, the power distribution system 222 can also distribute electrical power to the environmental regulation system 228 via an electrical conduit 290e. For example, the power distribution system 222 can deliver stored electrical power from the battery 224 and/or electrical power from the external power source 114. In some cases, the power distribution system 222 can selectively switch between delivering stored electrical power from the battery 224 and delivering electrical power from the external power source 114 (e.g., based on the amount of electrical power stored in the battery 224, the amount of electrical power allotted to each of the units 102, or other criteria). In a similar manner as described above, the functionality of the power distribution system 222 can be controlled by the electronic control system 250 based on these criteria.

In addition, the power distribution system 222 can also distribute electrical power to one or more power-consuming devices common to multiple units 102 and/or not specifically associated with a particular unit 102 (e.g., a "communal" amenity). As examples, the power distribution system 222 can be configured to distribute electrical power to elevators, light fixtures in common areas, appliances in common areas, etc.

As described herein, in some cases, the system 200 can be incorporated into a pre-existing multi-unit building. For example, sometime after a multi-unit building has been constructed, the multi-unit building can be modified or retrofitted to incorporate the system 200. This can be beneficial, for example, as it enables the owners or operators of pre-existing buildings to improve the operation of their buildings, even after the building has already been constructed.

As an example, FIG. 1 shows a multi-unit building 100a without an energy generation system 200. The multi-unit building 100a can be subsequently modified to incorporate the system 200. After modification, the multi-unit building 100a can be similar to the multi-unit building 100b shown in FIG. 2.

In some cases, the sewer line of a pre-existing multi-unit building can be modified to accommodate the system 200. For example, referring to FIG. 1, a pre-existing multi-unit building may have a pre-existing sewer line 152 that collects biological waste from the units 102, and routes the biological waste out of the building (e.g., to an external sewer 154). To accommodate the system 200, the sewer line can be diverted or "tapped" (e.g., along an intermediate portion) such that the biological waste is instead diverted to the system 200. Further, waste from the system 200 (e.g., liquid components from the anaerobic digestion tank 204) can be routed into the sewer line 154 (e.g., along a portion downstream of the diversion or tap) for removal from the multi-unit building. For example, the sewer line 154 shown in FIG. 1 can be diverted or tapped to form the sewer line 154 and the fluid conduit 280c shown in FIG. 2. This can be useful, for example, as it enables the system 200 to be retrofitted into a pre-existing multi-unit building without substantially modifying the existing infrastructure of the multi-unit building.

In some cases, the power distribution system of a pre-existing multi-unit building can be modified to accommodate the system 200. For example, referring to FIG. 1, a pre-existing multi-unit building may have pre-existing electrical conduits 116a that route electrical power from the external power source 114 into the multi-unit building 100a, and pre-existing electrical conduits 116b that route electrical power to each of the units 102. To accommodate the system 200, the electrical conduits 116a and 116b can be used to provide electrical power to the system 200 and to distribute electrical power from the system 200 to the units 102, respectively. For example, the electrical conduits 116a and 116b shown in FIG. 1 can be used as the electrical conduit 290c and 290d shown in FIG. 2, respectively. Similarly, this can be useful as it enables the system 200 to be retrofitted into a pre-existing multi-unit building without substantially modifying the existing infrastructure of the multi-unit building.

Figure 3:
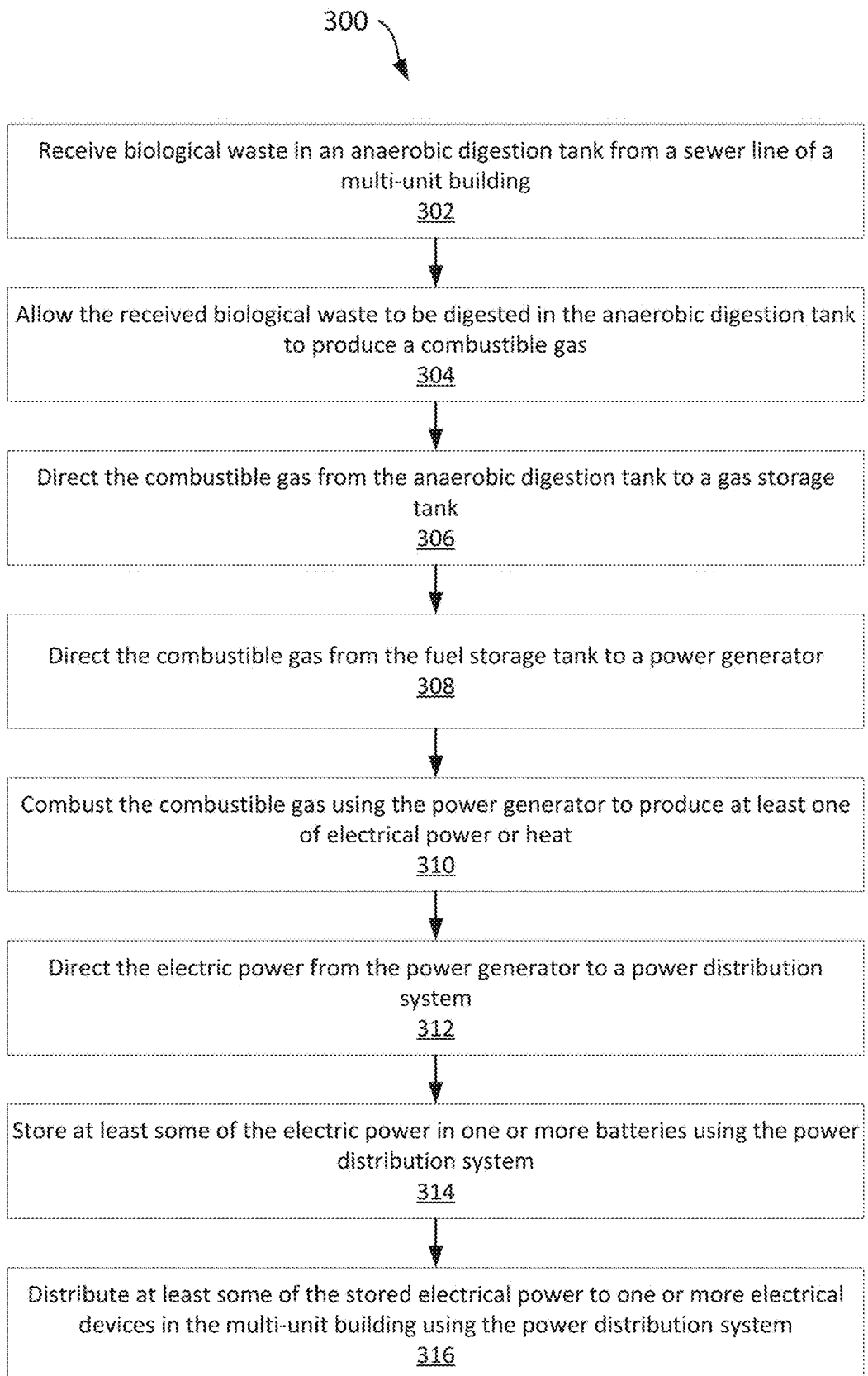
FIG. 3 is a flow chart diagram of an example process for generating energy (e.g., electrical power and/or heat) on-site a multi-unit building and distributing the generated energy.

An example process 300 for generating electrical power on-site a multi-unit building and distributing the generated electrical power is shown in FIG. 3. The process 300 can be implemented, for example, using the multi-unit building 100b and the energy generation system 200 shown in FIG. 2.

In the process 300, an anaerobic digestion tank receives biological waste from a sewer line of a multi-unit building (step 302). As an example, as described with respect to FIG. 2, an anaerobic digestion tank 204 can receive biological waste (e.g., urine, feces, food waste, etc.) from a sewer line 152. In some cases, the anaerobic digestion tank can be configured to receive biological waste a garbage conduit of a multi-unit building.

The received biological waste is allowed to be digested in the anaerobic digestion tank to produce a combustible gas (step 304). As an example, as described with respect to FIG. 2, the biological waste can be digested within the anaerobic digestion tank 204 to produce a combustible gas (e.g., through an anaerobic digestion process). The combustible gas can include methane, or can be predominantly methane (e.g., at least 50% by weight methane, at least 90% by weight methane, etc.). Microorganisms capable of digesting biological materials in an anaerobic environment, digestion-acceleration agents (e.g., glycol), and other substances can be introduced into the anaerobic digestion tank 204 to facilitate anaerobic digestion process (e.g., through a pressurized inlet valve 232).

The combustible gas is directed from the anaerobic digestion tank to a gas storage tank (step 306). As an example, as described with respect to FIG. 2, combustible gas can be directed from the anaerobic digestion tank 204 to a gas storage tank 212.

The combustible gas is directed from the gas storage tank to a power generator (step 308). As an example, as described with respect to FIG. 2, combustible gas can be directed from the gas storage tank 212 to the power/heat generator 216.

The combustible gas is combusted using the power generator to produce at least one of electrical power or heat (step 310). As an example, as described with respect to FIG. 2, combustible gas can be combusted using the power/heat generator 216 to produce electrical power, heat, or both.

The electrical power is distributed from the power generator to a power distribution system (step 312). As an example, as described with respect to FIG. 2, electrical power generated by the power/heat generator 216 can be distributed to a power distribution system 222.

The power distribution system stores at least some of the electrical power in one or more batteries (step 314). As an example, as described with respect to FIG. 2, the power distribution system 222 can store at least some of the electrical power in one or more batteries 224.

The power distribution system distributes at least some of the stored electrical power to one or more electrical devices in the multi-unit building (step 316). As an example, as described with respect to FIG. 2, the power distribution system 222 can store at least some of the electrical power stored in the batteries 224 to one or more electricity devices 112 in the units 102.

In some cases, some or all of the components used to perform the process 300 can be disposed within the multi-unit building. As an example, the anaerobic digestion tank, the gas storage tank, the power generator, and/or the power distribution system each can be disposed within the multi-unit building.

In some cases, the process 300 can be performed by retrofitting or modifying a pre-existing building. For instance, the sewer line of the multi-unit building can be a pre-existing conduit in the multi-building configured to receive the biological waste from at least one toilet in the building. Further, the process 300 can include installing a relay conduit extending between the sewer line and the anaerobic digestion tank to divert the biological waste from the sewer line to the anaerobic digestion tank. As an example, as described with respect to FIG. 2, a fluid conduit 280a can be installed to divert biological waste from a pre-existing sewer line 152 into the anaerobic digestion tank 204.

In some cases, the biological waste can include a solid portion and a liquid portion. Further, the process 300 can include separating at least some of the liquid portion from the solid portion (e.g., using a first outlet valve of the anaerobic digestion tank), and directing at least some of the liquid portion to a first waste conduit for removal from the multi-unit building (e.g., using the first outlet valve of the anaerobic digestion tank). As an example, as described with respect to FIG. 2, one or more filters 256 can be used to separate at least some of the liquid portion of the biological waste into a drainage channel 258. A flow regulation device 202c can be used to direct at least some of the liquid portion in the drainage channel 258 to a fluid conduit 280c for removal from the building.

In some cases, at least some of the solid portion can be directed to a second waste conduit for removal from the anaerobic digestion tank (e.g., using a second outlet valve). As an example, as described with respect to FIG. 2, an access port 208 (e.g., a valve, a drain, a channel, a door, a panel, or other port) can direct at least some of the solid portion of the biological waste to for removal from the anaerobic digestion tank 204.

In some cases, a mass of the biological waste contained within the anaerobic digestion tank can be determined (e.g., using a mass sensor). Further, a notification message can be transmitted to a remote device (e.g., using a transmitter) when the mass of the biological waste contained within the anaerobic digestion tank exceeds a threshold mass. As an example, as described with respect to FIG. 2, sensors 206 can be used to determine a mass of biological waste contained within the anaerobic digestion tank 204. These measurements can be transmitted to an electronic control system 250. Based on these measurements, the electronic control system 250 can transmit a notification to one or more client devices 252.

In some cases, a first pressure within the anaerobic digestion tank can be determined (e.g., using a first pressure sensor), and the combustible gas can be directed from the anaerobic digestion tank to the gas storage tank (e.g., using a first pump) when the first pressure exceeds a first threshold pressure. As an example, as described with respect to FIG. 2, sensors 206 can be used to determine the pressure within the anaerobic digestion tank 204. These measurements can be transmitted to an electronic control system 250. Based on these measurements, the electronic control system 250 can direct combustible gas from the anaerobic digestion tank 204 to the gas storage tank 212 by operating a fluid regulation device 202b.

In some cases, a second pressure within the gas storage tank can be determined (e.g., using a second pressure sensor), and the combustible gas can be directed from the gas storage tank to the power generator (e.g., using a second pump) when the second pressure exceeds a second threshold pressure. As an example, as described with respect to FIG. 2, sensors 214 can be used to determine the pressure within the gas storage tank 212. These measurements can be transmitted to an electronic control system 250. Based on these measurements, the electronic control system 250 can direct combustible gas from the gas storage tank 212 to the power/heat generator 216 by operating a fluid regulation device 202d.

In some cases, the threshold pressures can be user-specified parameter values that are provided to the electronic control system. As an example, as described with respect to FIG. 2, the electronic control system 250 can receive a first input from a user specifying the first threshold pressure, and operate the first pump (e.g., the fluid regulation device 202b) to direct the combustible gas from the anaerobic digestion tank to the gas storage tank when the first pressure exceeds a first threshold pressure. As another example, the electronic control system 250 can receive a second input from a user specifying the second threshold pressure, and operate the second pump (e.g., the fluid regulation device 202d) to direct the combustible gas from the gas storage tank to the power generator when the second pressure exceeds the second threshold pressure. In some cases, the second pressure can be greater than the first pressure (e.g., so that a greater amount of combustible gas is stored in the gas storage tank compared to the anaerobic digestion tank.

In some cases, a moisture filter can be used to remove moisture from the combustible gas as the combustible gas is directed from the anaerobic digestion tank to the gas storage tank. As an example, as described with respect to FIG. 2, one or more filters 210 can be used to remove moisture (or other contaminants) from the combustible gas.

In some cases, the power distribution system can be configured to receive external electrical power from a power source external to the multi-unit building. Further, a determination can be made regarding an amount of electrical power stored by the one or more batteries. Upon determining that the amount of electrical power stored by the one or more batteries is less than a threshold amount of electrical power, at least some of the received external electrical power can be distributed to one or more electrical devices in the multi-unit building. The power source external to the multi-unit building can an external power grid (e.g., a municipal or public power grid). As an example, as described with respect to FIG. 2, the power distribution system 222 can receive electrical power from an external power source 114. A determination can be made regarding an amount of electrical power stored by the one or more batteries 224 (e.g., using the electronic control system 250 and/or the power distribution system 222). Upon determining that the amount of electrical power stored by the one or more batteries 224 is less than a threshold amount of electrical power, at least some of the received external electrical power can be distributed to one or more electrical devices 112 in the units 102.

In some cases, this threshold amount of electrical power can be a user-specified parameter value that is provided to the electronic control system. As an example, as described with respect to FIG. 2, the electronic control system 250 can receive an input from a user specifying the threshold amount of electrical power, and operate the power distribution system (e.g., the power distribution system 222) to distribute at least some of the received external electrical power to one or more electrical devices in the multi-unit building when the amount of electrical power stored by the one or more batteries is less than the threshold amount of electrical power.

In some cases, the power distribution system can be configured to receive external electrical power from a power source external to the multi-unit building. Further, a determination can be made, for each unit of the multi-unit building, regarding a respective amount of electrical power consumed by the unit over a period of time. Upon determining that the amount of electrical power consumed by a particular unit exceeds a threshold amount of electrical power, at least some of the received external electrical power can be distributed to one or more electrical devices in that unit. As an example, as described with respect to FIG. 2, the power distribution system 222 can receive electrical power from an external power source 114. A determination can be made regarding an amount of electrical power consumed by each unit 102 over a period of time (e.g., using the electronic control system 250 and/or the power distribution system 222). Upon determining that the amount of electrical power consumed by a particular unit 102 exceeds a threshold amount of electrical power, at least some of the received external electrical power can be distributed to one or more electrical devices 112 in the units 102.

In some cases, this threshold amount of electrical power can be a user-specified parameter value that is provided to the electronic control system. As an example, as described with respect to FIG. 2, the electronic control system 250 can receive an input from a user specifying the threshold amount of electrical power, and operate the power distribution system (e.g., the power distribution system 222) to distribute at least some of the received external electrical power to one or more electrical devices in the particular unit when the amount of electrical power consumed by that unit over the period of time exceeds the threshold amount of electrical power.

In some cases, additional electrical power can generated using one or more additional power sources (e.g., solar, wind, kinetic, thermoelectric, etc.). This additional electrical power also can be stored and/or distributed by the power distribution system 222. As an example, as described with respect to FIG. 2, additional electrical power can be generated using a photovoltaic power generator (e.g., one or more solar panels) using light energy incident upon one or more photovoltaic modules of the photovoltaic power generator. The additional electrical power can be directed from the photovoltaic power generator to a power distribution system (e.g., the power distribution system 222). At least some of the additional electrical power can be stored in one or more batteries (e.g., batteries 224). Further, at least some of the stored additional electrical power can be distributed to one or more electrical devices (e.g., electrical devices 112) in the multi-unit building.

In some cases, at least some of the heat generated by the power generator can be distributed to one or more units of the multi-unit building. Further, in some cases, at least some of the heat generated by the power generator can be used to heat water in a water distribution system, and the heated water can be distributed to one or more units of the multi-unit building. As an example, as described with respect to FIG. 2, at least some of the heat generated by the power/heat generator 216 can be distributed to one or more units 102 using an environmental regulation system 228 (e.g., an HVAC systems). As another example, the environmental regulation system 228 can include water heaters or boilers to heat water using the heat generated by the power/heat generator 216, and distribute the heated water to one or more units 102.

In some cases, the electronic control system can be configured to regulate a temperature of the anaerobic digestion tank using a heating element of the anaerobic digestion tank. The heating element can configured to apply heat to the anaerobic digestion tank. As an example, as described with respect to FIG. 2, the anaerobic digestion tank 204 can include a heating element 230 (e.g., a heating coil) to regulate a temperature within the anaerobic digestion tank 204. The electronic control system 250 can control the operation of the heating element 230 (e.g., based on temperature measurements obtained by the sensors 206).

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, the electronic control system 250 and the client device 252 can be implemented using digital electronic circuitry, or in computer software, firmware, or hardware, or in combinations of one or more of them. In another example, the process 300 can be implemented using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 4:
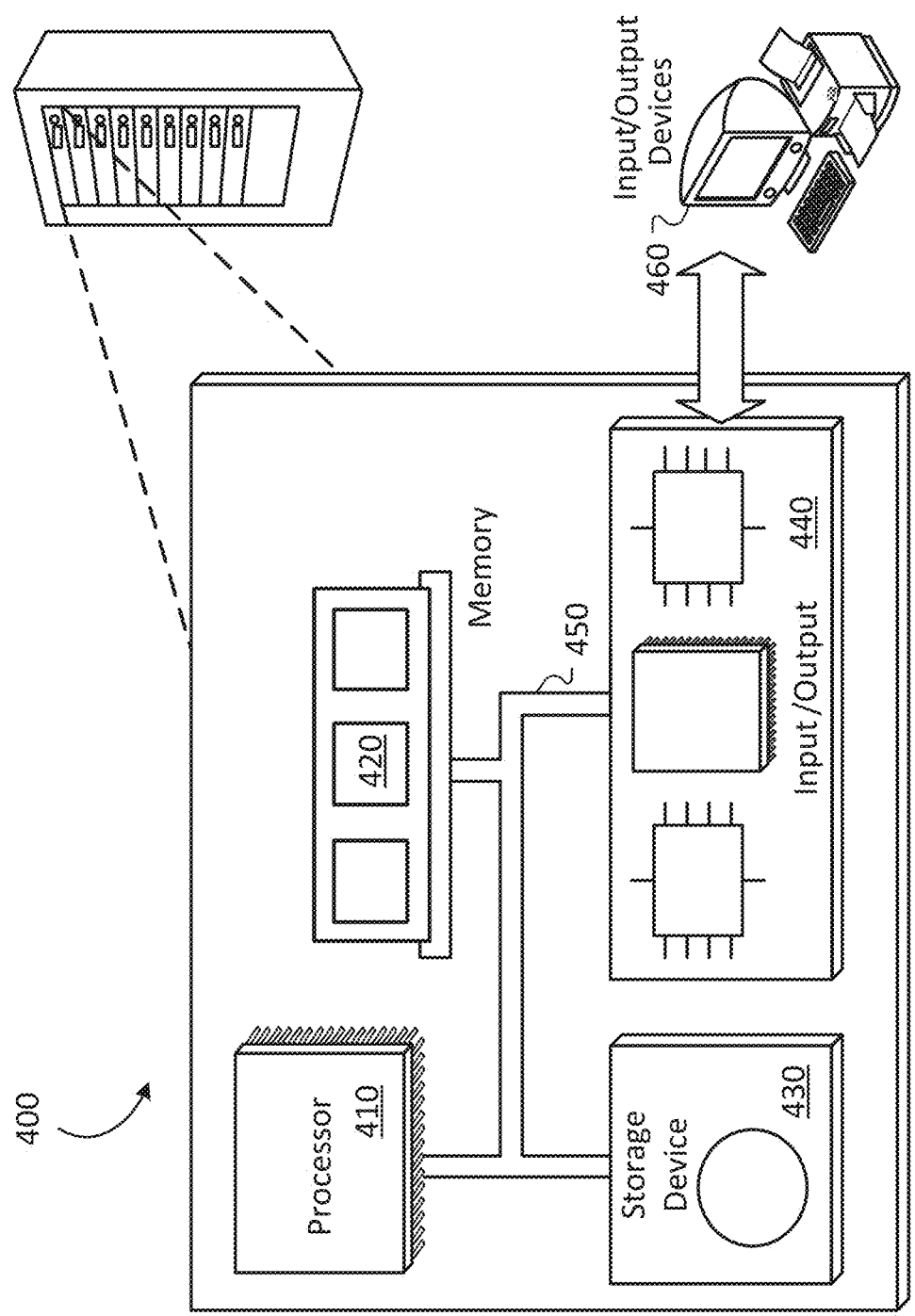
FIG. 4 is a diagram of an example computer system.

FIG. 4 shows an example computer system 400 that includes a processor 410, a memory 420, a storage device 430 and an input/output device 440. Each of the components

410, 420, 430 and 440 can be interconnected, for example, by a system bus 450. The processor 510 is capable of processing instructions for execution within the system 400. In some implementations, the processor 410 is a single-threaded processor, a multi-threaded processor, or another type of processor. The processor 410 is capable of processing instructions stored in the memory 420 or on the storage device 430. The memory 420 and the storage device 430 can store information within the system 400.

The input/output device 440 provides input/output operations for the system 400. In some implementations, the input/output device 440 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc. In some implementations, the input/output device can include driver devices configured to receive input data and send output data to other input/output devices, e.g., keyboard, printer and display devices 460. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of implementations have been described. Nevertheless, it will be understood that various modifications may be made without departing from the spirit and scope of the invention. Accordingly, other implementations are within the scope of the following claims.

What is claimed is:

1. A system comprising:
    an anaerobic digestion tank comprising:
        a chamber,
        a drainage channel disposed below the chamber,
        one or more gravity-fed filters separating the chamber from the drainage channel,
        a first outlet valve in fluid communication with the drainage channel, and
        a second outlet valve in fluid communication with the chamber;
    a gas storage tank in fluid communication with the anaerobic digestion tank;
    a power generator in fluid communication with the gas storage tank;
    a power distribution system in communication with the power generator; and
    an electronic control system in communication with the anaerobic digestion tank, the gas storage tank, power generator, and the power distribution system;
    wherein the anaerobic digestion tank is configured to:
        receive biological waste from a sewer line of a multi-unit building,
        separate, using the one or more gravity-fed filters, at least some of a liquid portion of the received biological waste from a solid portion of the received biological waste,
        direct, using the first outlet valve, at least some of the liquid portion of the received biological waste to a first waste conduit for removal from the multi-unit building,
        allow at least some of the solid portion of the received biological waste to be digested to produce a combustible gas, and
        direct, using the second outlet valve, at least some of the solid portion of the received biological waste to a second waste conduit for removal from the system,
    wherein the gas storage tank is configured to:
        receive the combustible gas from the anaerobic digestion tank, and
        store the combustible gas,
    wherein the power generator is configured to:
        receive the combustible gas from the gas storage tank, and
        combust the combustible gas to produce at least one of electrical power or heat, and
    wherein the power distribution system is configured to:
        receive the electrical power from the power generator,
        store at least some of the electrical power in one or more batteries, and
        distribute at least some of the stored electrical power to one or more electrical devices in the multi-unit building, and
    wherein the electronic control system is configured to control an operation of each of the anaerobic digestion tank, the gas storage tank, the power generator, and the power distribution system.

2. The system of claim 1, wherein the system is disposed within the multi-unit building.

3. The system of claim 1, wherein the combustible gas comprises methane.

4. The system of claim 1, wherein a sewer line of the multi-unit building is a pre-existing conduit in the multi-building configured to receive the biological waste from at least one toilet in the building, and wherein the anaerobic digestion tank is configured to receive biological waste from the sewer line through a relay conduit extending between the sewer line and the anaerobic digestion tank.

5. The system of claim 1, wherein the anaerobic digestion tank comprises a mass sensor configured to determine a mass of the biological waste contained within the anaerobic digestion tank, and
    wherein the system further comprises a transmitter configured to transmit a notification message to a remote device when the mass of the biological waste contained within the anaerobic digestion tank exceeds a threshold mass.

6. The system of claim 1, wherein the anaerobic digestion tank comprises:
    a first pressure sensor configured to determine a first pressure within the anaerobic digestion tank; and
    a second pressure sensor configured to determine a second pressure within the gas storage tank; and
    wherein the system further comprises:
        a first pump configured to direct the combustible gas from the anaerobic digestion tank to the gas storage tank when the first pressure exceeds a first threshold pressure, and
        a second pump configured to direct the combustible gas from the gas storage tank to the power generator when the second pressure exceeds a second threshold pressure.

7. The system of claim 6, wherein the electronic control system is configured to:
    receive a first input from a user specifying the first threshold pressure, operate the first pump to direct the combustible gas from the anaerobic digestion tank to the gas storage tank when the first pressure exceeds a first threshold pressure, receive a second input from the user specifying the second threshold pressure, and operate the second pump to direct the combustible gas from the gas storage tank to the power generator when the second pressure exceeds the second threshold pressure, wherein the second threshold pressure is greater than the first threshold pressure.

8. The system of claim 6, wherein the system further comprises one or more filters configured to remove at least one of moisture or contaminants from the combustible gas as the combustible gas is directed from the anaerobic digestion tank to the gas storage tank.

9. The system of claim 1, wherein the power distribution system is further configured to:

receive external electrical power from a power source external to the multi-unit building;

determine an amount of electrical power stored by the one or more batteries; and upon determining that the amount of electrical power stored by the one or more batteries is less than a threshold amount of electrical power, distributing at least some of the received external electrical power to one or more electrical devices in the multi-unit building.

10. The system of claim 9, wherein the electronic control system is configured to:

receive an input from a user specifying the threshold amount of electrical power, and operate the power distribution system to distribute at least some of the received external electrical power to the one or more electrical devices in the multi-unit building when the amount of electrical power stored by the one or more batteries is less than the threshold amount of electrical power.

11. The system of claim 1, wherein the power distribution system is further configured to:

Receive external electrical power from a power source external to the multi-unit building;

determine, for each unit of the multi-unit building, a respective amount of electrical power consumed by the unit over a period of time; and upon determining that the amount of electrical power consumed by a particular unit over the period of time exceeds a threshold amount of electrical power, distributing at least some of the received external electrical power to one or more electrical devices in that unit wherein the threshold amount of electrical power is less than a total amount of electrical power produced by the power generator.

12. The system of claim 11, wherein the electronic control system is configured to:

receive an input from a user specifying the threshold amount of electrical power, and operate the power distribution system to distribute at least some of the received external electrical power to one or more electrical devices in a particular unit when the amount of electrical power consumed by that unit over the period of time exceeds the threshold amount of electrical power.

13. The system of claim 1, further comprising a photovoltaic power generator including one or more photovoltaic modules, wherein the photovoltaic power generator is configured to generate additional electrical power using light energy incident upon the one or more photovoltaic modules, and wherein the power distribution system is further configured to:

receive the additional electrical power from the photovoltaic power generator, store at least some of the additional electrical power in the one or more batteries; and distribute at least some of the stored additional electrical power to one or more electrical devices in the multi-unit building.

14. The system of claim 1, further comprising an environmental regulation system configured to distribute at least some of the heat generated by the power generator to one or more units of the multi-unit building.

15. The system of claim 1, further comprising a water distribution system configured to:

receive at least some of the heat generated by the power generator, heat water using the received heat, and distribute the heated water to one or more units of the multi-unit building.

16. The system of claim 1, wherein the anaerobic digestion tank comprises a heating element configured to apply heat to the anaerobic digestion tank, and wherein the electronic control system is in communication with the heating element and configured to regulate a temperature of the anaerobic digestion tank using the heating element.

17. The system of claim 1, wherein the anaerobic digestion tank comprises an inlet valve, and wherein the anaerobic digestion tank is configured to receive a digestion-accelerating agent through the inlet valve.

18. The system of claim 1, wherein the anaerobic digestion tank is further configured to:

receive additional biological waste from a garbage conduit of the multi-unit building, and allow the received additional biological waste to be digested to produce the combustible gas.

19. The system of claim 1, wherein the power distribution system is further configured to:

allot, to each unit of the multi-unit building, a respective portion of the stored electrical power;

receive external electrical power from a power source external to the multi-unit building;

determine, for each unit of the multi-unit building, a respective amount of electrical power consumed by the unit over a period of time; and upon determining that the amount of electrical power consumed by a particular unit over the period of time exceeds the portion of the stored electrical power allotted to that unit, distributing at least some of the received external electrical power to one or more electrical devices in that unit.

20. A method comprising:

receiving, in an anaerobic digestion tank, biological waste from a sewer line of a multi-unit building;

separating, using one or more gravity-fed filters of the anaerobic digestion tank, at least some of a liquid portion of the received biological waste from a solid portion of the received biological waste;

directing, using a first outlet valve of the anaerobic digestion tank, at least some of the liquid portion of the received biological waste to a first waste conduit for removal from the multi-unit building, allowing at least some of the solid portion of the received biological waste to be digested in the anaerobic digestion tank to produce a combustible gas;

directing, using a second outlet valve of the anaerobic digestion tank, at least some of the solid portion of the received biological waste to a second waste conduit for removal from the system, directing the combustible gas from the anaerobic digestion tank to a gas storage tank;

directing the combustible gas from the gas storage tank to a power generator;

combusting the combustible gas using the power generator to produce at least one of electrical power or heat;

directing the electrical power from the power generator to a power distribution system;

storing, by the power distribution system, at least some of the electrical power in one or more batteries; and distributing, by the power distribution system, at least some of the stored electrical power to one or more electrical devices in the multi-unit building.

* * * * *

UNITED STATES PATENT AND TRADEMARK OFFICE
CERTIFICATE OF CORRECTION

| | | |
|---|---|---|
| PATENT NO. | : 11,192,814 B2 | Page 1 of 1 |
| APPLICATION NO. | : 16/762743 | |
| DATED | : December 7, 2021 | |
| INVENTOR(S) | : Ma | |

It is certified that error appears in the above-identified patent and that said Letters Patent is hereby corrected as shown below:

In the Specification

Column 1, Line 9, delete "which application" and insert --which--;

In the Claims

Column 29, Line 42, Claim 11, delete "Receive" and insert --receive--;

Column 29, Line 51, Claim 11, delete "unit" and insert --unit,--.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*